(12) United States Patent
Bitto et al.

(10) Patent No.: US 8,201,460 B2
(45) Date of Patent: Jun. 19, 2012

(54) MAGNET ASSEMBLY OF A MEASURING TRANSDUCER OF VIBRATION TYPE HAVING A MAGNET CUP AND RETAINING ASSEMBLY

(75) Inventors: Ennio Bitto, Aesch (CH); Gerhard Eckert, Grenzach-Wyhlen (DE); Dieter Mundschin, Liestal (CH)

(73) Assignee: Endress + Hauser Flowtec AG, Reinach (CH)

( * ) Notice: Subject to any disclaimer, the term of this patent is extended or adjusted under 35 U.S.C. 154(b) by 320 days.

(21) Appl. No.: 12/591,525

(22) Filed: Nov. 23, 2009

(65) Prior Publication Data
US 2010/0132480 A1   Jun. 3, 2010

Related U.S. Application Data

(60) Provisional application No. 61/193,425, filed on Nov. 28, 2008.

(30) Foreign Application Priority Data

Nov. 28, 2008 (DE) .................. 10 2008 044 186

(51) Int. Cl.
   *G01F 1/84* (2006.01)
(52) U.S. Cl. ................................ 73/861.357
(58) Field of Classification Search ................... None
   See application file for complete search history.

(56) References Cited

U.S. PATENT DOCUMENTS

| | | | |
|---|---|---|---|
| 3,949,606 A * | 4/1976 | Blancett | 73/861.87 |
| 4,895,031 A | 1/1990 | Cage | |
| 5,048,350 A | 9/1991 | Hussain | |
| 5,987,998 A | 11/1999 | Campbell | |
| 2004/0016303 A1 | 1/2004 | Loving | |

FOREIGN PATENT DOCUMENTS

| | | |
|---|---|---|
| DE | 199 36 008 A1 | 3/2001 |
| DE | 10 2007 062 397 A1 | 6/2009 |
| EP | 0 448 913 A1 | 10/1991 |
| EP | 1 253 409 A1 | 10/2002 |
| EP | 1 985 975 A2 | 10/2008 |
| WO | WO 88/02475 | 4/1988 |
| WO | WO 2007/043996 A1 | 4/2007 |

OTHER PUBLICATIONS

English translation of the International Preliminary Examination Report.

* cited by examiner

*Primary Examiner* — Harshad Patel
(74) *Attorney, Agent, or Firm* — Bacon & Thomas, PLLC

(57) ABSTRACT

A magnet assembly includes: a magnetic field delivering, especially rod-shaped, permanent magnet; a retaining assembly fixedly connected with the permanent magnet and having a retaining head facing the permanent magnet and serving for holding the permanent magnet, and a retaining bolt affixed to the retaining head; and a magnet cup having a cup floor and a cup wall extending from the cup floor. The retaining head of the retaining assembly is at least partially accommodated in a passageway provided in the cup floor, so that an outer contact surface of the retaining head and an inner contact surface of the passageway contact one another to form a force-based interlocking between magnet cup and retaining assembly. The magnet assembly is, especially, provided for application as an oscillation transducer and/or for use in a measuring transducer of vibration type.

15 Claims, 6 Drawing Sheets

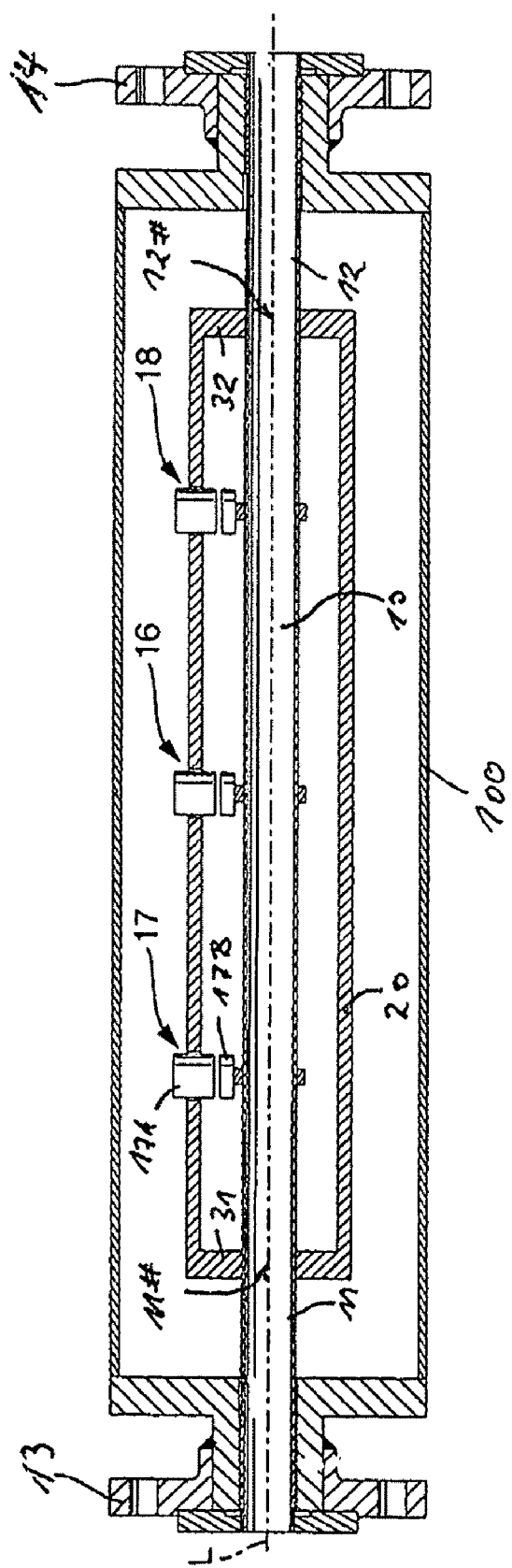

MAGNET ASSEMBLY OF A MEASURING TRANSDUCER OF VIBRATION TYPE HAVING A MAGNET CUP AND RETAINING ASSEMBLY

CROSS-REFERENCE TO RELATED APPLICATION

This application is a Nonprovisional which claims the benefit of U.S. Provisional Application No. 61/193,425, filed on Nov. 28, 2008.

TECHNICAL FIELD

The invention relates to a magnet assembly, especially a magnet assembly suitable for an oscillation transducer and/or for a measuring transducer of the vibration type, and includes a permanent magnet providing a magnetic field, a retaining assembly securely connected to the permanent magnet, and a magnet cup. Furthermore, the invention relates to a measuring transducer of the vibration type for a medium flowing in a pipeline, wherein the measuring transducer is equipped with at least one such magnet assembly.

BACKGROUND DISCUSSION

In industrial measurement technology, especially also in connection with the control and monitoring of automated manufacturing processes, for ascertaining characteristic measured variables of media, for example, liquids and/or gases, flowing in a process line, for example, a pipeline, often measuring systems are used, which by means of a measuring transducer of the vibration type and, connected thereto, driving, and evaluating, electronics (most often accommodated in a separate electronics housing) induce reaction forces, for example, Coriolis forces, in the flowing medium and produce, derived from these, a measurement signal correspondingly representing the at least one measured variable, for example, mass flow, density, viscosity or some other process parameter. Measuring systems of this kind, which are often formed by means of an inline measuring device in compact construction with integrated measuring transducer, such as, for instance, a Coriolis mass flow meter, have been known for a long time and have proven themselves in industrial use. Examples of such measuring systems having a measuring transducer of vibration type, or also individual components thereof, are described e.g. in WO-A 88/02475, WO-A 88/03642, WO-A 99 40 394, WO-A 08/059,015, WO-A 08/013,545, WO-A 07/043,996, WO-A 01 02 816, WO-A 00/12971, WO-A 00 14 485, U.S. Pat. Nos. 7,392,709, 7,360,451, 7,340,964, 7,299, 699, 7,213,469, 7,080,564, 7,077,014, 7,073,396, 7,040,179, 7,017,424, 6,920,798, 6,883,387, 6,860,158, 6,840,109, 6,758,102, 6,691,583, 6,666,098, 6,651,513, 6,557,422, 6,519,828, 6,397,685, 6,378,364, 6,330,832, 6,223,605, 6,168,069, 7,337,676, 6,092,429, 6,047,457, 5,979,246, 5,945,609, 5,796,012, 5,796,011, 5,796,010, 5,731,527, 5,691,485, 5,610,342, 5,602,345, 5,531,126, 5,476,013, 5,398,554, 5,301,557, 5,291,792, 5,287,754, 4,823,614, 4,777,833, 4,738,144, US-A 20080250871, US-A 20080223150, or US-A 20080223149, US-A 2008/0141789, US-A 2008/0047361, US-A 2007/0186685, US-A 2007/0151371, US-A 2007/0151370, US-A 2007/0119265, US-A 2007/0119264, US-A 2006/0201260, U.S. Pat. No. 6,311, 136, JP-A 9-015015, JP-A 8-136311, EP-A 317 340 or the not pre-published German patent application 102007062397.8. Each of the therein illustrated, measuring transducers comprises at least one, essentially straight, or at least one, curved, measuring tube for conveying the medium, which can, in given cases, also be extremely cold or extremely hot. Furthermore, each of the measuring transducers shown in U.S. Pat. Nos. 5,291,792, 5,945,609, 7,077,014, US-A 2007/0119264, WO-A 01 02 816 or also WO-A 99 40 394 includes a supplemental transducer housing (especially a supplemental transducer housing mounted directly to the inlet tube piece and to the outlet tube piece), which surrounds the measuring tube and the counteroscillator coupled thereto, as well as the exciter mechanism and sensor arrangement, while, for example, in the measuring transducer shown in U.S. Pat. No. 4,823,614, the transducer housing is quasi composed of the counteroscillator, or, in other words, transducer housing and counteroscillator are one and the same structural unit.

During operation of the measuring system, the at least one measuring tube is caused to vibrate for the purpose of generating oscillatory forms influenced by the medium flowing through the tube. For exciting oscillations of the at least one measuring tube, measuring transducers of the vibration type additionally include an exciter mechanism actuated by an appropriately conditioned, electric, driver signal, e.g. a controlled current and/or a controlled voltage, generated by the mentioned driver electronics. This excites the measuring tube to bending oscillations in the wanted mode by means of at least one electro-mechanical, especially electrodynamic, oscillation exciter, through which excitation current flows during operation. Furthermore, such measuring transducers include a sensor arrangement with oscillation sensors, especially electrodynamic oscillation sensors, for at least point-wise registering of oscillations, especially oscillations in the Coriolis mode, at the inlet, and outlet, sides of the at least one measuring tube and for producing electric sensor signals influenced by the process parameters to be registered, such as mass flow or density. In addition to the oscillation sensors provided for registering vibrations of the measuring tube, the measuring transducer can have still more sensors, as also provided in EP-A 831 306, U.S. Pat. Nos. 5,736,653, 5,381, 697, or WO-A 01/02 816, among others, especially serving to register rather secondary measurement variables, such as e.g. temperature, acceleration, expansion, stress, etc., and arranged on, or in the vicinity of, the inner part formed, in any case, of measuring tube, counteroscillator, as well as the exciter mechanism and sensor arrangement attached thereto.

As excited oscillation form—the so-called wanted mode—in the case of measuring transducers with a curved, e.g. U, V, or Ω shaped measuring tube, normally the eigenoscillation form is selected, in which the measuring tube moves like a pendulum at least partially at a lowest natural resonance frequency about a longitudinal axis of the measuring transducer, in the manner of a cantilever fixed at an end, as a result of which mass flow dependent, Coriolis forces are induced in the medium flowing through the measuring tube. These in turn lead to the fact that, superimposed on the excited oscillations of the wanted mode, in the case of curved measuring tubes, thus pendulum-like cantilever oscillations, are bending oscillations of the same frequency corresponding to at least one, also natural, second oscillation form, the so-called Coriolis mode. In the case of measuring transducers with curved measuring tubes, these cantilever oscillations, caused by Coriolis forces, correspond usually with that eigenoscillation form in which the measuring tube also executes rotational oscillations about a vertical axis oriented perpendicular to the longitudinal axis. In the case of measuring transducers with straight measuring tubes, for the purpose of generating mass flow dependent, Coriolis forces, often a wanted mode is selected in which the measuring tube at least partially executes bending oscillations essentially in a single plane of oscillation, such that the oscillations in the Coriolis mode are formed, accordingly, as bending oscillations coplanar with the oscillations of the wanted mode, and are of the same oscillation frequency. As a result of the superimposing of wanted mode and Coriolis mode, the oscillations of the vibrating measuring tube registered by the sensor arrangement at the inlet and outlet sides of the measuring tube have a mass flow dependent, measurable, phase difference. Normally, the measuring tubes of such measuring transducers, e.g. those used in Coriolis mass flow meters, are excited during operation at an instantaneous, natural resonance frequency of the oscillation form selected for the wanted mode, especially at oscillation amplitude controlled to be constant. Since this resonance frequency especially is also dependent on the instantaneous density of the medium, commercially available Coriolis mass flow meters can measure, in addition to mass flow, also the density of media flowing in the measuring tube. Furthermore, it is also possible, as shown for example in U.S. Pat. Nos. 6,651,513 or 7,080,564, using measuring transducers of the vibration type, to directly measure the viscosity of the medium flowing through the measuring tube, for example based on an exciter power required for exciting the oscillations. In the case of measuring transducers with two measuring tubes, these are normally linked into the process line via a distributor piece on the inlet side, extending between the measuring tubes and a connecting flange on the inlet side, as well as via a distributor piece on the outlet side, extending between the measuring tubes and a connecting flange on the outlet side.

In the case of measuring transducers having a single measuring tube, such normally communicates with the process line via an essentially straight piece of connecting tube which opens into the inlet side of the measuring tube, as well as an essentially straight piece of connecting tube which opens into the outlet side of the measuring tube. Furthermore, each of the illustrated measuring transducers having a single measuring tube includes, composed of a single piece or multiple parts, at least one tubular, box-shaped, or plate-shaped counteroscillator, which, with formation of a first coupling zone, is coupled to the inlet side of the measuring tube, and, with formation of a second coupling zone, is coupled to the outlet side of the measuring tube, and which in operation essentially rests or oscillates equally and oppositely to the measuring tube, that is, with the same frequency and opposite phase. The inner part of the measuring transducer, formed by measuring tube and counteroscillator, is normally held in a protective, measuring transducer housing alone by means of the two pieces of connecting tube, via which the measuring tube communicates with the process line during operation, especially in a way enabling oscillation of the inner part relative to the measuring tube. In the case of measuring transducers shown in, for example, U.S. Pat. Nos. 5,291,792, 5,796,010, 5,945,609, 7,077,014, US-A 2007/0119264, WO-A 01 02 816, or also WO-A 99 40 394, having a single, essentially straight, measuring tube, the latter and the counteroscillator are oriented essentially coaxially to one another, as is common in conventional measuring transducers. In standard measuring transducers of the previously named type, the counteroscillator normally is also essentially tubular, and is formed as an essentially straight hollow cylinder, which is arranged in the measuring transducer such that the measuring tube is at least partially surrounded by the counteroscillator. Used as materials for such counteroscillators are normally relatively cost-efficient types of steel, such as structural steel, or free-machining steel, especially when titanium, tantalum, or zirconium are used for the measuring tube.

The exciter mechanism of measuring transducers of the type being discussed normally has at least one, usually electrodynamic, magnet assembly, serving as oscillation exciter, and acting differentially on the at least one measuring tube, and the, in given cases, present, counteroscillator, or the, in given cases, present, other measuring tube, while the sensor arrangement includes a electrodynamic magnet assembly on the inlet side of the measuring tube, serving as an inlet-side oscillation sensor, as well as at least one magnet assembly on the outlet side of the measuring tube, of essentially the same construction, serving as an outlet-side oscillation sensor. Usually, at least the magnet assemblies serving as oscillation sensors are essentially of the same construction. Such magnet assemblies serving as oscillation transducers of standard measuring transducers of vibration type are formed by means of a magnetic coil (in the case of measuring transducers with one measuring tube and a counteroscillator coupled thereto, the coil is normally mounted on the latter), as well as by means of an elongated, especially rod-shaped, permanent magnet, which, serving as an armature, interacts with the at least one magnetic coil, especially plunging into the coil, and which is mounted correspondingly on the measuring tube to be vibrated. This has the advantage, for example, that, by means of the magnet assemblies, the oscillatory movements between the vibrating measuring tube and its counterpart, that is, the, in given cases, present counteroscillator or the, in given cases, present, other measuring tube, can be differentially registered, or produced, as the case may be. The permanent magnet and the magnetic coil serving as exciter, or sensor, coil are, in such case, normally oriented essentially coaxially to one another. Additionally, in the case of conventional measuring transducers, the magnet assembly serving as oscillation exciter is normally formed and positioned in the measuring transducer in such a way that it acts essentially centrally on the at least one measuring tube. In such case, the magnet assembly serving as oscillation exciter is, as shown, for example, also in the measuring transducers disclosed in U.S. Pat. Nos. 5,796,010, 6,840,109, 7,077,014 or 7,017,424, usually mounted at least pointwise along an imaginary central peripheral line of the measuring tube on its outer side. Alternatively to oscillation exciters formed by means of a magnet assembly acting centrally and directly on the measuring tube, exciter mechanisms formed, as provided in U.S. Pat. Nos. 6,557,422, 6,092,429 or 4,823,614 among others, for example, by means of two magnet assemblies mounted not in the center of the measuring tube, but, instead, shifted, respectively, toward its inlet and outlet sides, can also be used, or, as provided in U.S. Pat. Nos. 6,223,605 or 5,531,126, among others, exciter mechanisms formed, for example, by means of a magnet assembly working between the, in given cases, present counteroscillator and the measuring transducer housing, are also used.

In the case of measuring transducers of the type being discussed, it is, as mentioned also in U.S. Pat. Nos. 6,047,457 or 6,920,798, among others, common to connect magnetic coils and the corresponding permanent magnet of the magnet assemblies serving as oscillation transducers—it may be an oscillation exciter or an oscillation sensor—to ring- or washer-shaped, especially metal, mounting elements attached to the measuring tube. These mounting elements securely surround the measuring tube essentially along circumferential lines of the measuring tube. The particular mounting element, as provided in U.S. Pat. Nos. 6,047,457, 7,299,699, US-A 2006/0201260, U.S. Pat. Nos. 5,610,342, or 6,519,828, among others, can be fixed to the measuring tube by pressing externally, by hydraulic pressing or rolling from inside of the measuring tube, or by thermal shrink fit, especially in such a manner that it is lastingly subjected to elastic or mixed plastic-elastic deformations, and as a result, is permanently prestressed radially with respect to the measuring tube.

In standard measuring transducers of the vibration type, the magnet assemblies serving as oscillation sensors are, as already indicated, often essentially of the same construction as the at least one magnet assembly serving as the oscillation exciter, insofar as they work according to the same operating principle. Accordingly, the magnet assemblies of such a sensor arrangement are also mostly formed, in each case, of: at least one magnetic coil—normally fixed on a, in given cases, present counteroscillator—and, at least at times, passed through by a variable magnetic field, and thus at least periodically provided with an induced measurement voltage; as well as a rod-shaped permanent magnet, mounted on the measuring tube and interacting with the at least one magnetic coil, and providing the magnetic field. Additionally, each of the aforementioned coils is connected with the mentioned operating and evaluation electronics of the in-line measuring device by means of at least one pair of electric, connecting lines, which are normally run along the shortest route possible from the coils, over the counteroscillator, to the transducer housing.

In the case of magnet assemblies of the aforementioned type, for the purpose of homogenizing the magnetic field flowing through the coil and the permanent magnet, as well as for the purpose of avoiding disturbing stray fields, the permanent magnet is normally placed within a magnet cup composed at least partially of magnetically conductive material, and is secured to a cup base, from which extends an essentially tubular, especially circular cylindrically formed wall of the magnet cup. Normally, the permanent magnet is arranged essentially in a center of the cup base, and usually affixed to this such that permanent magnet and cup wall are oriented coaxially to one another.

For securing the permanent magnet and magnet cup in magnet assemblies of the type being discussed, as shown in WO-A 88/02475 for example, a clamp screw is fed through a bore provided in the permanent magnet, and through a corresponding bore in the cup base, and is tightened with an appropriate clamp nut. However, such a clamp screw—especially the screw-head, ultimately forming the free end of the permanent magnet—can undesirably deform, and, in this respect, disturb, the magnetic field carried in the magnet assembly.

To avoid such disturbances of the magnetic field, in magnet assemblies of standard measuring transducers of the vibration type, as also shown in WO-A 07/043,996 or WO-A 00/12971, among others, the permanent magnet and cup base are often connected with one another by a material bond, for instance by brazing or welding, if necessary also using a sleeve pressed onto the permanent magnet, and moderating between the permanent magnet and the braze material. Furthermore, it is quite common to fix the permanent magnet to the cup base using an adhesive bond. However, as also mentioned in WO-A 00/12971 or U.S. Pat. No. 6,883,387 among others, magnet assemblies of the type being discussed can be exposed to significant stresses resulting from very high (>200° C.) or very low (<−50° C.) operating temperatures, and/or resulting from high acceleration forces (>10 G), such that the material bonds formed between the permanent magnet and cup base, either through adhesive or brazed connections, must fulfill very high quality requirements, especially with regard to fatigue strength under operating conditions.

A disadvantage of such connections using material bonds between the permanent magnet and cup base, however, is that especially also due to the mounting position of the permanent magnet within the magnet cup, as well as the very small dimensions of the permanent magnet and magnet cup, the application of the substances ultimately forming the material bonds, for instance the braze material or the adhesive, on the one hand, and, on the other hand, the highly precise orientation of the permanent magnet within the magnet cup, can be related to considerable difficulties, and in that respect can be very complicated. Additionally, due to the most often very different materials for the permanent magnet and cup base, especially with regard to workability and required fatigue strength over a broad thermal and/or mechanical stress range, really well-suited braze material or adhesive is not readily available, or else is very expensive.

SUMMARY OF THE INVENTION

An object of the invention is to improve magnet assemblies of the aforementioned kind suitable for measuring transducers of the vibration type, such that, on the one hand, their assembly is simplified, and, on the other hand, also, respectively, the fatigue strength of such magnet assemblies and their operating temperature range are increased.

For achieving the object, the invention resides in a magnet assembly, especially a magnet assembly for an oscillation transducer and/or for a measuring transducer of the vibration type, wherein the magnet assembly includes:
  a permanent magnet, especially a rod-shaped permanent magnet, which provides a magnetic field;
  a retaining assembly, especially a retaining assembly formed as clamping jaws, which securely holds the permanent magnet, especially one securely holding the permanent magnet by means of force-based interlocking, and/or shape-based interlocking, and/or material bonding, wherein the retaining assembly includes
    a retaining head, facing the permanent magnet, for holding the permanent magnet, especially a retaining head formed at least partially as an outer cone, and
    a retaining bolt, secured to the retaining head, especially a retaining bolt having exterior threading and/or a lengthwise slotted segment adjoining the retaining head; and
  a magnet cup, wherein the magnet cup includes
    a cup base, and
    a cup wall extending from the cup base, especially a cup wall that is formed essentially circular cylindrically and/or tubularly;
  wherein the retaining head of the retaining assembly is accommodated at least partially by a passageway provided in the cup base, especially a passageway formed at least partially as an inner cone; and
  wherein an outer contact surface of the retaining head and an inner contact surface of the passageway contact one another, resulting in the formation of a force-based interlocking between the magnet cup and retaining assembly, especially in a manner which expands the passageway and/or elastically deforms the cup base.

Furthermore, the invention resides in a measuring transducer of the vibration type for a medium flowing in a pipeline, which transducer includes at least one, at least at times vibrating, measuring tube for conveying the medium to be measured, as well as at least one oscillation transducer, especially serving as an electrodynamic oscillation exciter or electrodynamic oscillation sensor, secured to the at least one measuring tube, for vibrations of the at least one measuring tube, wherein the at least one oscillation transducer is formed by means of the abovementioned magnet assembly.

In a first embodiment of the magnet assembly of the invention, it is provided that the retaining bolt of the retaining assembly has external threading, and that the retaining head of the retaining assembly is held pressed against the cup base by means of a clamping nut screwed onto the retaining bolt. Developing this embodiment of the invention further, it is additionally provided, that a resilient, or spring, element is placed between the clamping nut and cup base, especially a resilient ring or a Belleville spring.

In a second embodiment of the magnet assembly of the invention, it is provided, that the retaining head is formed by means of at least two or more head parts, each in the form of a clamping jaw. Developing this embodiment of the invention further, it is additionally provided, that the permanent magnet is placed with one of its ends between the at least two head parts, and that the at least two head parts are each held pressed against the permanent magnet, with formation of a force-based interlocking between the permanent magnet and retaining head, especially such an interlocking produced from the interaction of the clamping nut, the passageway, and the at least two head parts.

In a third embodiment of the magnet assembly of the invention, it is provided, that the force-based interlocking between magnet cup and retaining assembly is produced by means of thermal shrinking, or shrink fitting, of the magnet cup onto the retaining assembly, especially the retaining head.

In a fourth embodiment of the magnet assembly of the invention, it is provided, that permanent magnet and retaining head are affixed to one another, especially by means of releasable, force-based interlocking, and/or by means of shape-based interlocking, and/or by means of bonding produced between materials, especially by brazing or adhesive bonding.

In a fifth embodiment of the magnet assembly of the invention, it is provided, that the cup wall of the magnetic cup has at least one slot, especially a slot extending to an edge of the cup wall distal with respect to the cup base.

In a sixth embodiment of the magnet assembly of the invention, it is provided, that the permanent magnet is composed, at least partially, especially predominantly or entirely, of a rare earth, especially as NdFeB, SmCo, or the like; and/or
   wherein the permanent magnet is composed at least partially, especially predominantly or entirely, of ferrite or AlNiCo.

In a seventh embodiment of the magnet assembly of the invention, it is provided, that the magnet cup is composed, at least partially, especially predominantly or entirely, of steel, especially free-machining steel or structural steel; and/or the magnet cup is composed at least partially, especially predominantly or entirely, of ferrite.

In a first embodiment of the measuring transducer of the invention, it is provided, that the magnet assembly is mechanically coupled with the at least one measuring tube via retaining bolts.

In a second embodiment of the measuring transducer of the invention, the at least one oscillation transducer further includes a cylindrical coil exposed to the magnetic field of the permanent magnet.

One among many advantages of the invention is that the magnet assembly enables the use of a measuring transducer of vibration type, equipped with said magnet assembly, in an in-line measuring device, especially a Coriolis mass flow measuring device, a density measuring device, a viscosity measuring device, or the like, for measuring and/or monitoring at least one parameter, especially mass flow m, density, $\rho$, and/or viscosity, $\eta$, of a medium flowing in a pipeline, even in the case of extreme operating temperatures of, at least at times, more than 200° C. and/or, at least at times, less than −50° C. In addition, the construction or mounting of magnet assemblies of the type under discussion can be greatly simplified, and thus the total production costs of measuring transducers of vibration type are reduced.

BRIEF DESCRIPTION OF THE DRAWINGS

The invention, and advantageous embodiments thereof, will now be described in further detail on the basis of an example of an embodiment illustrated in the figures of the drawing; in the figures, equal parts are provided with equal reference characters. In case helpful for avoiding clutter, already used reference characters are omitted in subsequent figures. The figures of the drawing show as follows:

FIG. 1b shows schematically in a sectioned side view, a measuring transducer of vibration type suitable for an in-line measuring device of FIG. 1a;

DETAILED DISCUSSION IN CONJUNCTION WITH THE DRAWINGS

Figure 1A:
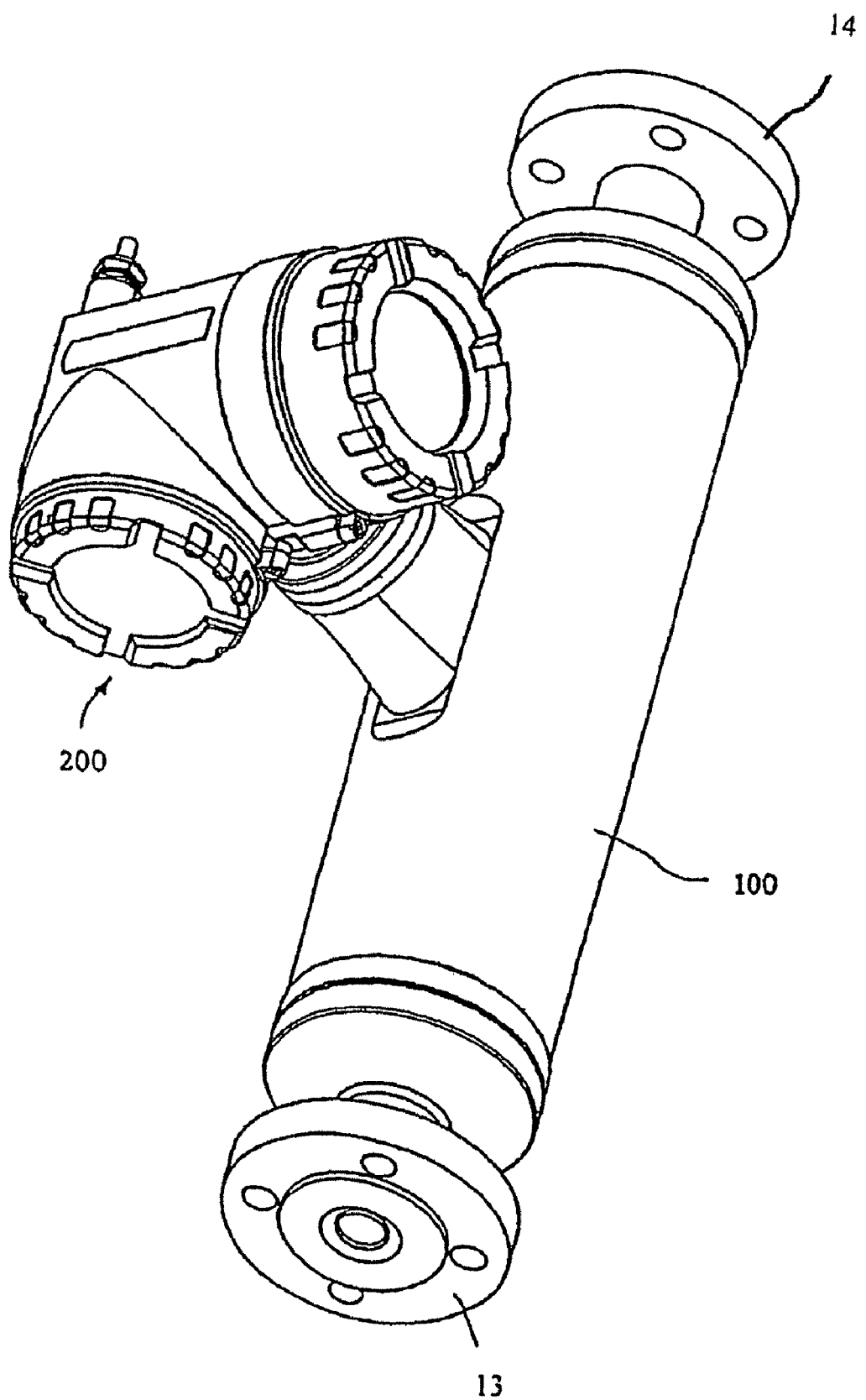
FIG. 1a shows schematically in a perspective side view, an in-line measuring device for media flowing in pipelines.

FIG. 1a shows a measuring system insertable in a process line (not shown), for instance, a pipeline of an industrial plant, for example, a measuring system in the form of a Coriolis mass flow measuring device, density measuring device, viscosity measuring device, pressure measuring device or the like, serving for measuring and/or monitoring at least one physical measured variable, for example, mass flow, density, viscosity, etc., of a medium flowing in the process line, for example, a hot medium at more than 200° C. or a cold medium at less than −50° C. The measuring system—here formed as an in-line measuring device of compact construction—includes, connected to the process line at an inlet end as well as at an outlet end, a measuring transducer of the vibration type, through which, during operation, the medium to be measured flows. The transducer is electrically connected to a driver electronics of the measuring system serving to actuate the measuring transducer, as well as to an evaluation electronics of the measuring system for processing a primary signal of the measuring transducer, and, if necessary during operation, for communicating with the driver electronics. The evaluation electronics, during operation, delivers the measurement values representing the at least one parameter. The driver electronics and the evaluation electronics, as well as additional electronics components serving the operation of the measuring system, such as, for example, energy supply circuits and/or communications circuits serving to connect to a superordinated measurement data processing system and/or a fieldbus, are located in an appropriate electronics housing 200, especially an impact, and/or explosion, resistant electronics housing.

FIG. 1b shows, schematically and greatly simplified, an example of an embodiment of such a measuring transducer of vibration type. The measuring transducer serves to produce, in a medium flowing through it, mechanical reaction forces, e.g. mass flow dependent, Coriolis forces, density dependent, inertial forces, and or viscosity dependent frictional forces, which interact with the measuring transducer in a way that can be measured, especially registered by sensors. Derived from these reaction forces, e.g. a mass flow m, a density ρ, and/or a viscosity η can be measured in manner known to those skilled in the art. The measuring transducer includes a transducer housing 100, as well as an inner part arranged in the transducer housing 100 and actually effecting the physical to electrical transducing of the at least one parameter to be measured.

For conveying the medium, the inner part includes at least one—in the example of an embodiment shown in FIG. 1b, essentially straight—measuring tube 10, which, during operation, is caused to vibrate and, in such case, is continuously elastically deformed oscillatingly around a static, rest position. It is to be noted here that, although the measuring transducer in the example of the embodiment shown in FIG. 2 has a single, straight measuring tube, and, at least in its mechanical assembly as well as its functional principle, is like those in the initially mentioned EP-A 317 340, U.S. Pat. Nos. 7,299,699, 7,073,396, 7,040,179, 7,017,424, 6,840,109, 6,691,583, 6,651,513, 6,397,685, 6,330,832, 6,047,457, 5,979,246, 5,945,609, 5,796,012, 5,796,010, 5,691,485, 5,531,126, 5,476,013, 5,398,554, 5,291,792, 4,823,614, other measuring transducers of vibration type can, of course, serve for implementing the invention, especially those with more than one measuring tube, and/or with bent measuring tubes. For example, the at least one measuring tube, and, as a result, also an imaginary central axis running within the lumen of the measuring tube, can be formed such that it is at least sectionally essentially S, Ω, or U shaped, or, such that it is at least sectionally essentially V shaped, as shown e.g. in U.S. Pat. Nos. 6,860,158, 6,666,098, 7,213,469, or 7,360,451. Examples of other measuring tube forms suitable for implementing the invention are described, moreover, in, among others, the initially mentioned U.S. Pat. Nos. 5,287,754, 5,602,345, 5,796,011, 6,311,136, 6,758,102, 5,731,527, 5,301,557, or 6,920,798.

During operation of the measuring transducer, the measuring tube 10, as is common in the case of such measuring transducers, is excited to bending oscillations in the so-called wanted mode—for example, at an excitation frequency $f_{exc}$ corresponding essentially to a natural resonance frequency—such that it deflects oscillatingly about an imaginary axis of bending oscillations—here, essentially parallel to, or coinciding with, a longitudinal axis L of the measuring transducer imaginarily connecting its inlet and outlet ends—, at least partially essentially in accordance with a natural first eigenoscillation form. For the operationally provided case, in which medium is flowing in the process line, and thus the mass flow m is different from zero, Coriolis forces are induced in the flowing medium by means of the vibrating measuring tube in the previously described manner. These forces, in turn, act on the measuring tube 10, and cause in it an additional deformation which can be registered by sensors, essentially corresponding to a second, natural form of eigenoscillation. An instantaneous feature of this so-called Coriolis mode, superimposed on the excited wanted mode having the same frequency, is, in such case, especially as regards its amplitude, also dependent on the instantaneous mass flow m. The second form of eigenoscillation can be, as is common in the case of such measuring transducers with straight measuring tubes, e.g. the eigenoscillation form involving an anti-symmetric bending oscillation mode essentially coplanar with the wanted mode.

For minimizing disturbing influences acting on the measuring tube 10, as well as also for reducing oscillatory energy released by the measuring transducer to the connected process line, there is provided in the measuring transducer, additionally, a counteroscillator 20. This is, as shown in FIG. 1b, arranged in the measuring transducer laterally spaced from the measuring tube 10 and affixed to the measuring tube 10 at two locations, forming thus a first coupling zone 11# on the inlet side—essentially defining an inlet end of the measuring tube 10—and a second coupling zone 12# on the outlet side—essentially defining an outlet end of the measuring tube 10. The counteroscillator 20, which, in the illustrated example of an embodiment, extends essentially parallel to the measuring tube 10 and, in given cases, is arranged also coaxially therewith, can be embodied, for example, tubularly or also essentially box shaped. In the example of an embodiment shown here, the counteroscillator 20 is held by means of at least one, inlet-side, first coupler 31 on the inlet end 11# of the measuring tube 10 and by means of at least one, outlet-side, second coupler 32 (especially a second coupler 32 essentially identical to the coupler 31) on the outlet end 12# of the measuring tube 10. Couplers 31, 32 can be, in such case, e.g. simple node plates, which are secured in corresponding manner on the inlet side and on the outlet side in each case to measuring tube 10 and to counteroscillator 20, for instance, by pressing on, and/or soldering on, of corresponding metal bodies according to the initially mentioned U.S. Pat. No. 6,047,457 or U.S. Pat. No. 6,168,069.

As shown schematically in FIG. 1b, the measuring tube 10 is additionally connected, via a straight, first connecting tube piece 11 opening on the inlet side in the region of the first coupling zone 11# and via a straight, second connecting tube piece 12, especially a second connecting tube piece 12 essentially identical to the first connecting tube piece 11, opening on the outlet side in the region of the second coupling zone 12#, correspondingly to the process line (not shown), respectively, supplying, and draining, the medium, wherein an inlet end of the inlet-side connecting tube piece 11 forms, essentially, the inlet end of the measuring transducer and an outlet end of the outlet-side connecting tube piece 12 the outlet end of the measuring transducer. In advantageous manner, measuring tube 10 and the two connecting tube pieces 11, 12 can be embodied as one-piece, so that e.g. a single tubular stock, or semifinished part, can serve for their manufacture. Instead of this, that measuring tube 10, inlet tube piece 11 and outlet tube piece 12 are each formed by segments of a single, one piece tube, these can, in case required, however, also be produced by means of individual, subsequently joined together, e.g. welded together, stock, or semifinished parts. For manufacture of the measuring tube 10, moreover, essentially any of the materials usual for such measuring transducers, such as e.g. steel, Hastelloy, titanium, zirconium, tantalum, etc., can be used.

As directly evident from the combination of FIGS. 1a and 1b, the transducer housing 100, which, especially in comparison to the measuring tube 10, is bending, and torsionally, stiff, is affixed, especially rigidly, to an, as regards the first coupling zone #11, distal inlet end of the inlet-side connecting tube piece 11 as well as to an, as regards the first coupling zone #11, distal outlet end of the outlet-side connecting tube piece 12. As a result, thus the entire inner part is not only completely encased by the transducer housing 100, but, also, as a result of its eigenmass and the spring action of the two connecting tube pieces 11, 12, also held oscillatably in the transducer housing 100. In addition to the accommodating of the inner part, the transducer housing 100 can additionally also serve to hold the electronics housing 200 of the inline measuring device with therein accommodated, driver, and evaluation, electronics. For the case, in which the measuring transducer is to be assembled releasably with the process line, for example, a process line in the form of a metal pipeline, additionally, the inlet-side connecting tube piece 11 is provided on its inlet end with a first connecting flange 13 of the measuring transducer and the outlet-side connecting tube piece 12 is provided on an outlet end with a second connecting flange 14 of the measuring transducer. The connecting flanges 13, 14 can, in such case, such as quite usual in the case of measuring transducers of the described type, also be integrated at least partially terminally in the transducer housing 100. In case required, the connecting tube pieces 11, 12 can, moreover, however, also be connected directly with the process line, e.g. by means of welding or hard soldering (also called brazing).

For exciting mechanical oscillations of the measuring tube 10, especially the bending oscillations in the wanted mode, as well as of the, in given cases, present counteroscillator 20, the measuring transducer comprises additionally at least one oscillation transducer serving as oscillation exciter 16 and acting, here, centrally on the measuring tube. Other suitable positions for the oscillation transducer serving as oscillation exciter are shown e.g. in the initially mentioned U.S. Pat. Nos. 6,557,422, 6,092,429, 4,823,614, 6,223,605 or 5,531,126. The oscillation exciter serves, operated by an exciter signal delivered from the driver electronics and, in given cases, correspondingly conditioned in interaction with the evaluating electronics, e.g. an exciter signal having a controlled electrical current and/or a controlled voltage, to convert electrical exciter energy $E_{exc}$, fed by means of the driver electronics, into an exciter force $F_{exc}$ acting on the measuring tube 10, e.g. with pulse shape, or harmonically, and deflecting such in the above-described manner. Suitable driver electronics for tuning the exciter energy $E_{exc}$ are sufficiently known to those skilled in the art and shown e.g. in U.S. Pat. Nos. 4,777,833, 4,801,897, 4,879,911 or 5,009,109. The exciter force $F_{exc}$ can, such as usual in the case of such measuring transducers, be bidirectional or unidirectional and can be tuned in manner known to those skilled in the art e.g. by means of an electrical current, and/or voltage, control circuit as regards its amplitude and e.g. by means of a phases control loop as regards its frequency.

In an additional embodiment of the invention, the at least one measuring tube is excited during operation by means of the oscillation exciter 16, at least at times, in a wanted mode, in which it, at least partially—especially predominantly or exclusively—executes bending oscillations about the imaginary oscillation axis connecting inlet and outlet ends of the measuring tube imaginarily with one another, for example, with a single one, and/or a lowest, of its resonance frequencies. The bending oscillations of the measuring tube have in such case in the region of the inlet-side coupling zone 11# defining the inlet-side end of the measuring tube an inlet-side oscillation node and in the region of the outlet-side coupling zone 11# defining the outlet-side end of the measuring tube an outlet-side oscillation node. In the case of the example of an embodiment illustrated in FIG. 2, the measuring tube 10 executes the bending oscillations relative to the counteroscillator 20 and longitudinal axis L.

For registering oscillations of the measuring tube 10, the measuring transducer includes additionally at least one additional oscillation transducer serving as first oscillation sensor 17 and arranged, here, on the inlet side of the measuring tube for producing at least a first primary signal $s_1$ of the measuring transducer representing vibrations of the measuring tube 10. As usual in the case of measuring systems of the type being discussed, the measuring transducer can additionally have at least one additional, second oscillation sensor 18 placed, for example, on the outlet side on the measuring tube and/or constructed essentially equally to the oscillation sensor 17 for delivering at least one further, second primary signal $s_2$ of the measuring transducer representing, for example, outlet-side vibrations of the at least one measuring tube 10. In the example of an embodiment shown here, the oscillation transducer serving as first oscillation sensor 17 on the inlet side and the oscillation transducer serving as second oscillation sensor 18 on the outlet side are so arranged on the at least one measuring tube that the measuring transducers can be used, for example, also in a measuring system in the form of a Coriolis mass flow measuring device. The two oscillation transducers serving as oscillation sensors 17, 18, especially transducers formed with essentially equal construction, are, in such case, arranged in advantageous manner on one and the same side of the measuring tube 10 and, in such case, so placed in the measuring transducer spaced from each of the two coupling zones 11#, 12#, that they in each case have essentially the same distance to the midlength of the measuring tube 10, or to the, in each case, nearest of the two coupling zones 11#, 12#.

The aforementioned oscillation transducers are electrically connected with the mentioned driver electronics, or the mentioned evaluation electronics, of the in-line measuring device by means of corresponding connecting lines, which, in turn, are led, at least sectionally, within the transducer housing; compare, for this, especially, also the initially mentioned patent applications US-A 20080250871, US-A 20080223150, or US-A 20080223149 of the assignee. The connecting lines can, in such case, be embodied, at least partially, as electrical line wires encased, at least sectionally, in an electrical insulation, e.g. line wires in the form of "twisted pair" lines, flat ribbon cables and/or coaxial cables. Alternatively thereto or in supplementation thereof, the connecting lines can at least sectionally also be formed by means of conductive traces of an, especially flexible, in given cases, lacquered, circuit board.

In the case of the measuring transducer of the invention, it is additionally provided, that at least one—, in given cases, also each—of the aforementioned oscillation transducers 16, 17, 18 serving as oscillation sensor, or as oscillation exciter, is formed by means of a magnet assembly 5 (->16, 17, or 18) secured, for example, on the measuring tube 10 and having a permanent magnet 51a placed in a magnet cup.

The permanent magnet, at least partially of ferromagnetic material, can, for example, be made of a magnetic ceramic, such as, for instance, ferrite and/or "rare earth", especially NdFeB (neodynium iron boron) or SmCo (samarium cobalt), etc., while the magnet cup 51b can be composed, at least partially, of a magnetically conductive, metal alloy, for example, thus of AlNiCo (aluminum nickel cobalt) or a steel, such as, for instance, a free-machining steel or a structural steel. Starting from the cup floor 51b', there extends additionally a, for example, essentially circular cylindrically and/or tubularly embodied, cup wall 51b" of the magnet cup 51b. The permanent magnet 51a —here embodied to be elongated and/or rod-shaped —is, in turn, —such as presented schematically in FIGS. 2a and 2b —placed within the magnet cup 51b on a cup floor 51b' of the magnet cup 51b, for example, essentially in a center of the cup floor 51b', with the cup floor 51b' being secured, for example, directly to the measuring tube 10. For the already mentioned case, in which the cup wall 51b" of the magnet cup 51b is essentially circular cylindrically and/or tubularly embodied, according to another, further development of the invention, it is additionally provided, that permanent magnet 51a and cup wall 51b" are oriented extending essentially coaxially relative to one another. Additionally, it can be of advantage, especially for the purpose of reducing disturbing influences of external magnetic fields on the magnet assembly and/or for the purpose of suppressing disturbing eddy currents within the magnet assembly, to form, in the permanent magnet and/or, such as schematically presented in FIG. 1, in the cup wall 51b" of the magnet cup, at least one slot 51c"; compare, in this connection, also the initially mentioned German patent application 102007062397.8.

The oscillation transducer formed by means of the aforementioned magnet assembly 5 includes additionally a coil facing the permanent magnet and, here, correspondingly affixed to the counteroscillator 20; alternatively thereto, the coil 52 can, however, also be affixed to the counteroscillator 20 and in corresponding manner the permanent magnet 51a correspondingly therewith affixed to the measuring tube 10.

The coil 52, implemented, for example, in the form of a cylindrical coil, is arranged as near as possible to the permanent magnet 51a, and, indeed, such that it is exposed to its magnetic field. For the case, in which the magnet assembly 51 serves as an oscillation sensor, there is, as a result of the relative movement of permanent magnet 51a and coil 52, induced in the latter a variable, measurement voltage. For the other case, in which the magnet assembly 51 serves as an oscillation exciter, there is produced, by means of the exciter signal applied to the coil 52, the exciter force $F_{exc}$ effecting the vibrations of the measuring tube. Coil and permanent magnet can be so placed in the measuring transducer and so oriented relative to one another e.g. that the permanent magnet plunges into the coil in the manner of a plunging armature and is moved within such back and forth. In an additional embodiment of the invention, permanent magnet 51a and coil 52 of the at least one oscillation sensor are oriented extending essentially coaxially relative to one another.

In the magnet assembly of the invention, there is provided, additionally, a retaining assembly 51c serving for affixing the—in the here illustrated example of an embodiment rather elongated, or rod-shaped—permanent magnet in the magnet cup. At least in the installed state, or in the case of assembled magnet assembly 5, the retaining assembly 51c is fixedly connected with the permanent magnet 51a, for instance, by force, and/or shape, interlocking and/or by material bond. The retaining assembly 51c includes a retaining head 51c' facing the permanent magnet and contacting it for holding the permanent magnet, as well as a retaining bolt 51c" affixed to the retaining head. The retaining bolt is additionally suitably affixed to the measuring tube 10 at its end facing away from the retaining head.

Serving for holding the magnet assembly to the measuring tube can be, for example, a securement element SE pushed onto the measuring tube 10 and tightly encircling, especially completely encircling, the measuring tube essentially along one of its imaginary, peripheral lines, especially a metal and/or essentially washer shaped, securement element. Construction and application of such securement elements for magnet assemblies are known to those skilled in the art, for example, also from the initially mentioned U.S. Pat. Nos. 6,047,457, 6,519,828 or 7,299,699. Serving as material for the securement element 30 can be e.g. a metal alloy, for instance, of titanium or a steel, compatible with the retaining bolt, or with the solder or braze material serving for its affixing, or a corresponding ceramic. Retaining bolt and securement element can be connected with one another, for example, by bonding, for instance, by means of soldering or brazing.

Likewise, the retaining head 51c' and the retaining bolt 51c" can also be affixed to one another by means of material bonded connection, such as, for instance, soldering, brazing or welding or adhesive; retaining head 51c' and retaining bolt 51c" can, however, e.g. also be embodied as a monolithic component manufactured from one piece kept free of joints. Equally, permanent magnet 51a and retaining head 51c' can be affixed to one another by means of shape interlocking and/or by means of material bond, especially such produced by solder or braze connection or adhesive bond. Alternatively thereto, the permanent magnet 51a and the retaining head 51c' can, however, also be embodied as one-piece, for example, in shape of a monolithic, sintered part or the permanent magnet can be fixedly connected with the retaining assembly 51c by means of an, especially releasable, force-based interlocking, formed between this and the retaining head.

Figure 2A:
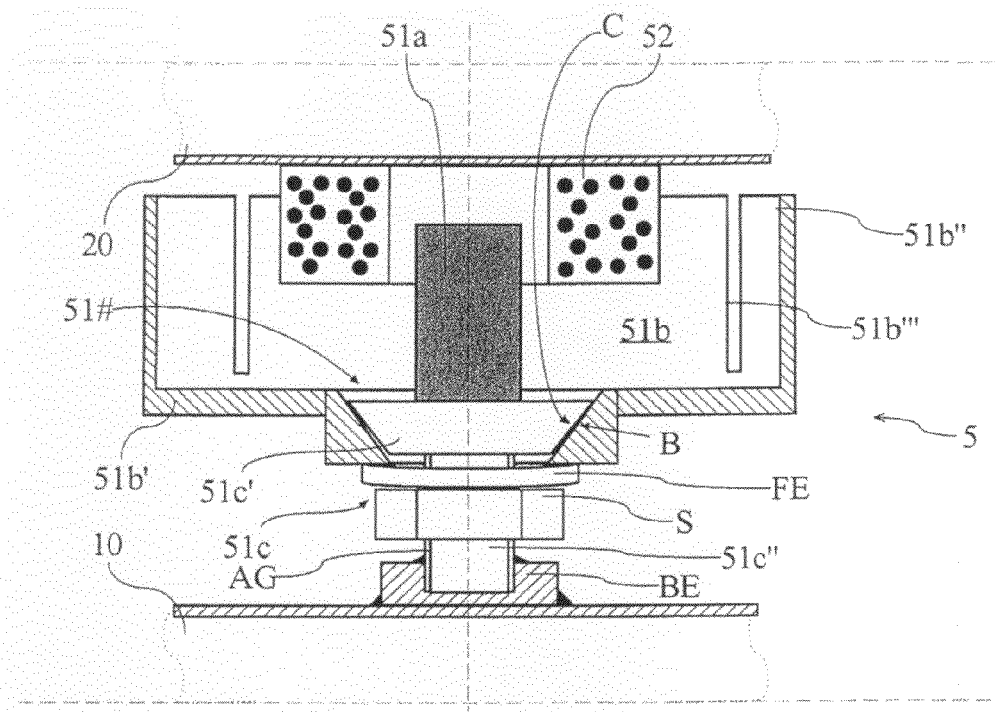
FIGS. 2a and 2b show schematically in a sectioned side view (2a), or in a plan view (2b), a magnet assembly for a measuring transducer of FIG. 1b.
Figure 4:
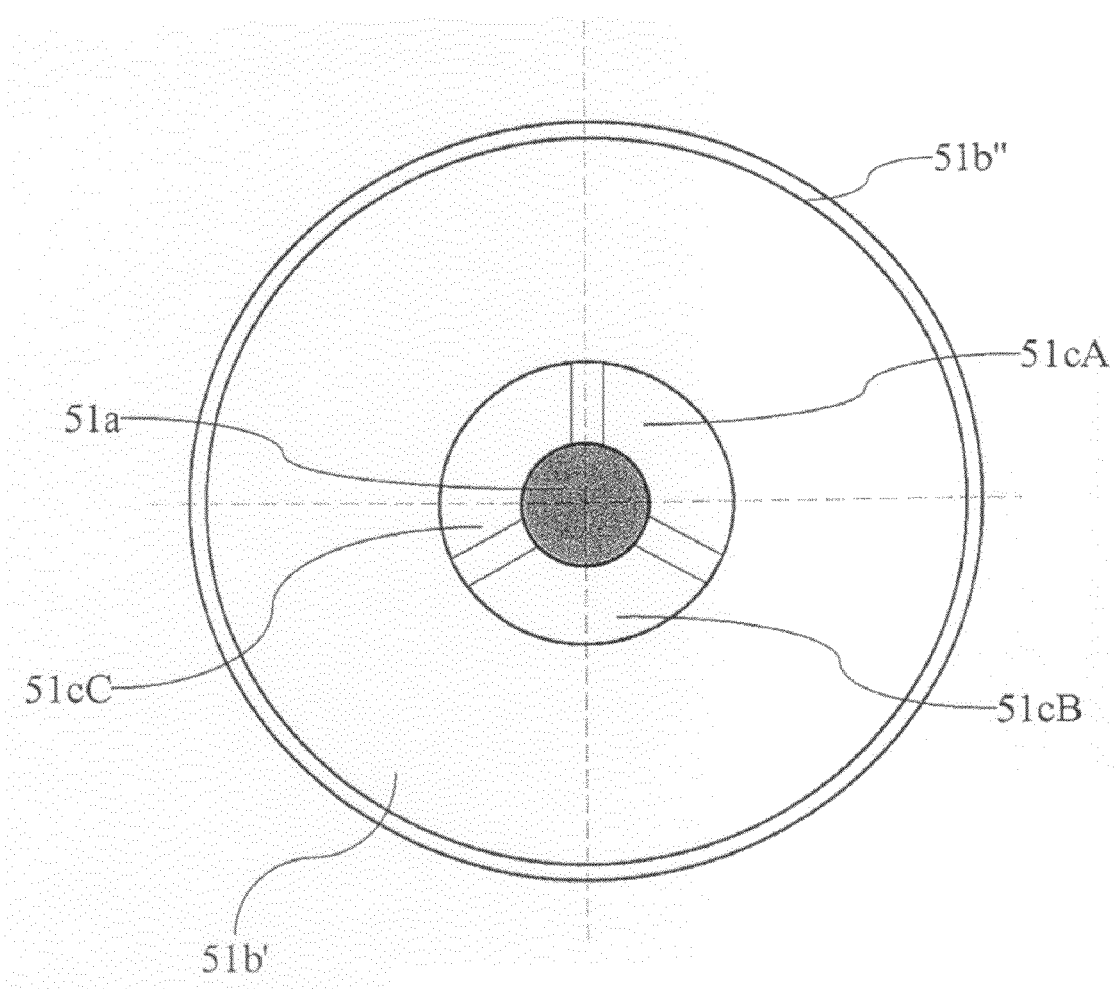
FIG. 4 shows schematically in plan view, yet another variant of a magnet assembly suited for a measuring transducer of FIG. 1b.

As schematically presented in FIGS. 2a, b or also in FIGS. 4a, b, the, for example, essentially frustoconically shaped or also circular cylindrically embodied, retaining head 51c' of the magnet assembly 5 of the invention is additionally accommodated, at least partially, in a passageway 51# provided in the cup floor 51b, and, indeed, such that an outer contact surface C of the retaining head 51c' and an inner contact surface B of the passageway 51# contact one another for forming a force-based interlocking between magnet cup 51b and retaining assembly 51c. The force-based interlocking between magnet cup 51b and retaining assembly 51c can be produced, for example, by thermal shrink fitting of the magnet cup on the earlier in the passageway correspondingly positioned, retaining head and/or by mixed plastic-elastic deformation of the magnet cup, for instance, by pressing of the same against the retaining head provided in the passageway, for example, also according to one of the methods for the affixing of metal bodies proposed in the initially mentioned U.S. Pat. Nos. 6,047,457, 6,519,828 or 7,299,699. For increasing the strength of the shape-interlocking between magnet cup and retaining assembly, additionally, such as, for example, also provided in U.S. Pat. No. 7,299,699, supplementally also shape interlocking creating contours can be formed into the contact surfaces of passageway 51# and/or the retaining head.

In another embodiment of the invention, such as schematically presented in FIG. 2a, the retaining head is at least partially embodied as an outer cone and the passageway provided in the cup floor at least partially as an inner cone, and, indeed, in such a manner, that the mutually contacting contact surfaces of retaining head, or passageway, are essentially complementary relative to one another. At least in the case of this embodiment, the retaining bolt of the retaining assembly is provided with an external thread ET. Additionally, the retaining head in the case of this embodiment of the invention is, such as schematically presented in FIG. 2a and especially also in combination with FIG. 4 directly recognizable, held pressed, by means of a clamping nut CN screwed on the retaining bolt, against the cup floor 51b', in given cases, also in a manner widening the passageway 51#, or deforming the cup floor, elastically. Serving for increasing the vibration resistance of the screwed connection can be, in such case, additionally a resilient, or spring, element RE, for example, embodied as an annular spring or as a Belleville spring, placed between clamping nut and cup floor. Of course, the section of the retaining bolt equipped with the external thread ET is so dimensioned, that, by interaction of clamping nut, cup floor and retaining head, a sufficiently large clamping force can be produced.

Figure 2B:
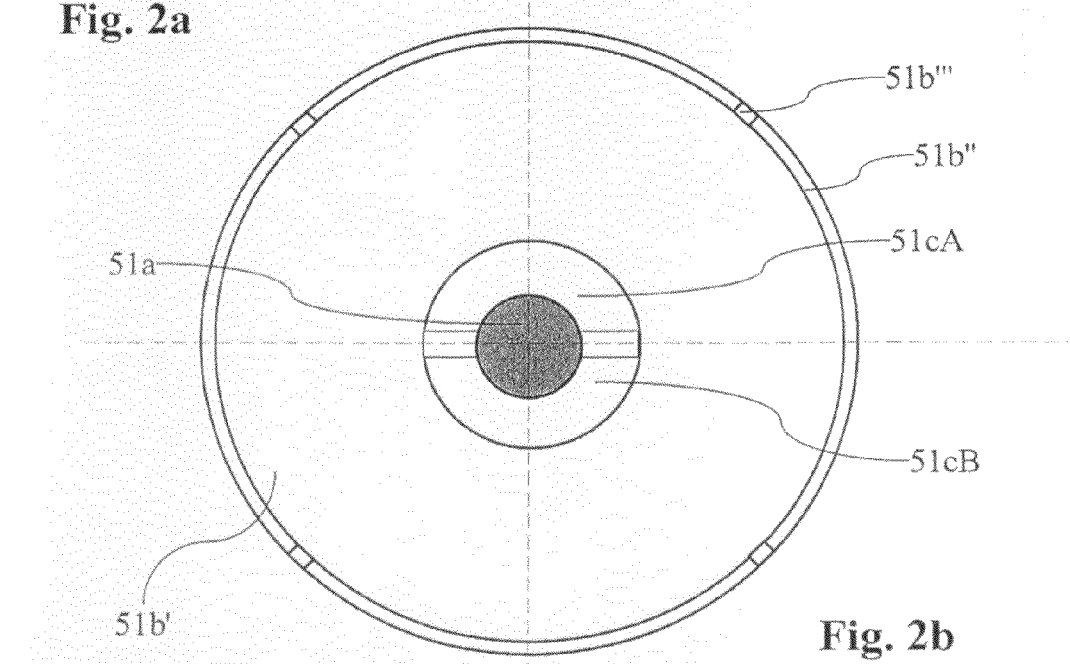
Figure 3A:
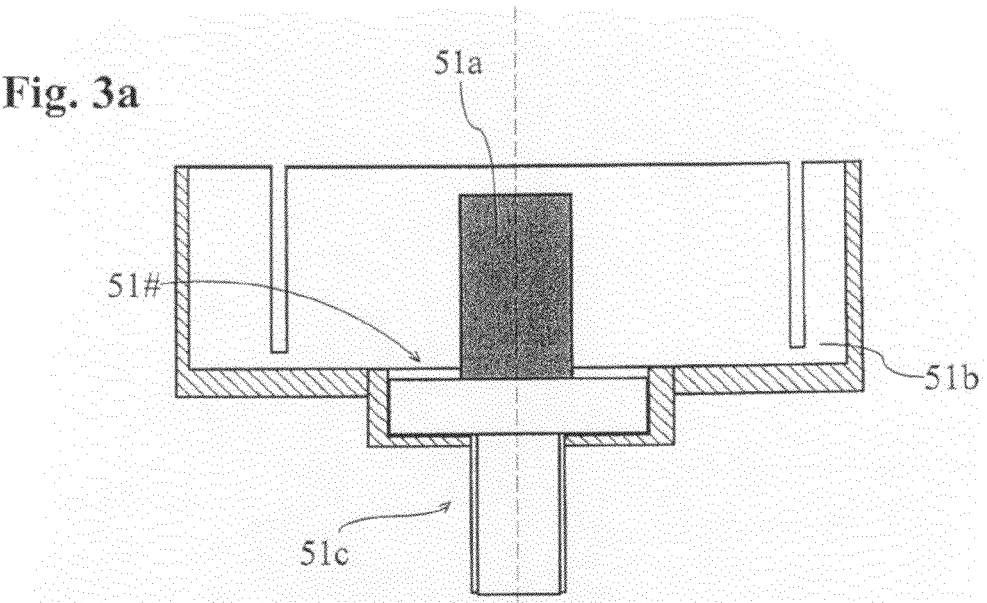
FIGS. 3a and 3b show schematically in partially sectioned side view (3a), or in a plan view (3b), another variant of a magnet assembly suited for a measuring transducer of FIG. 1b.
Figure 3B:
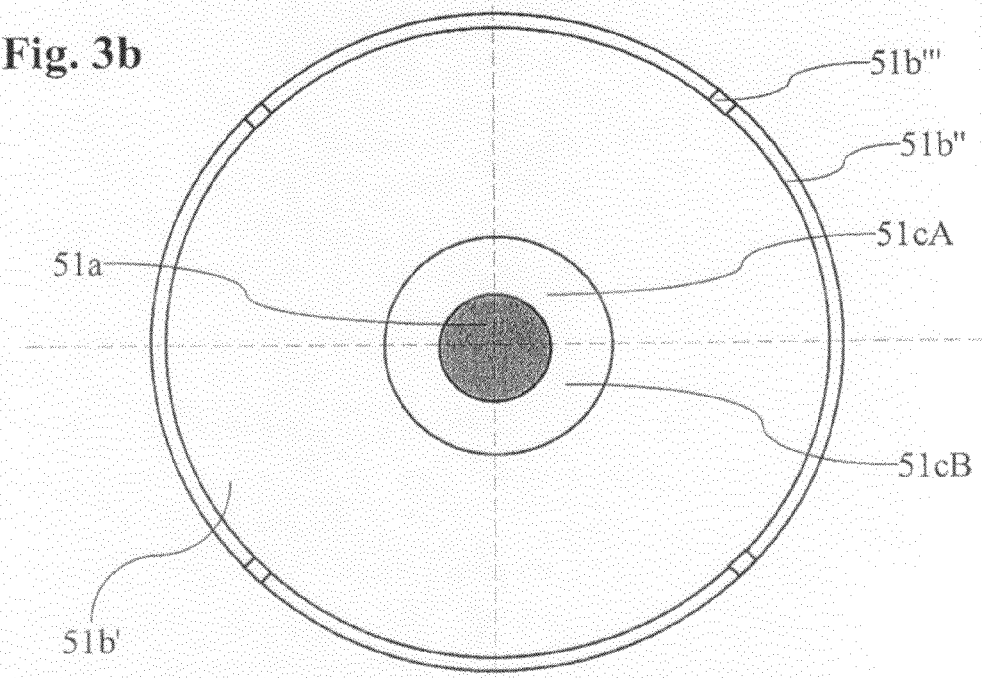
Figure 5:
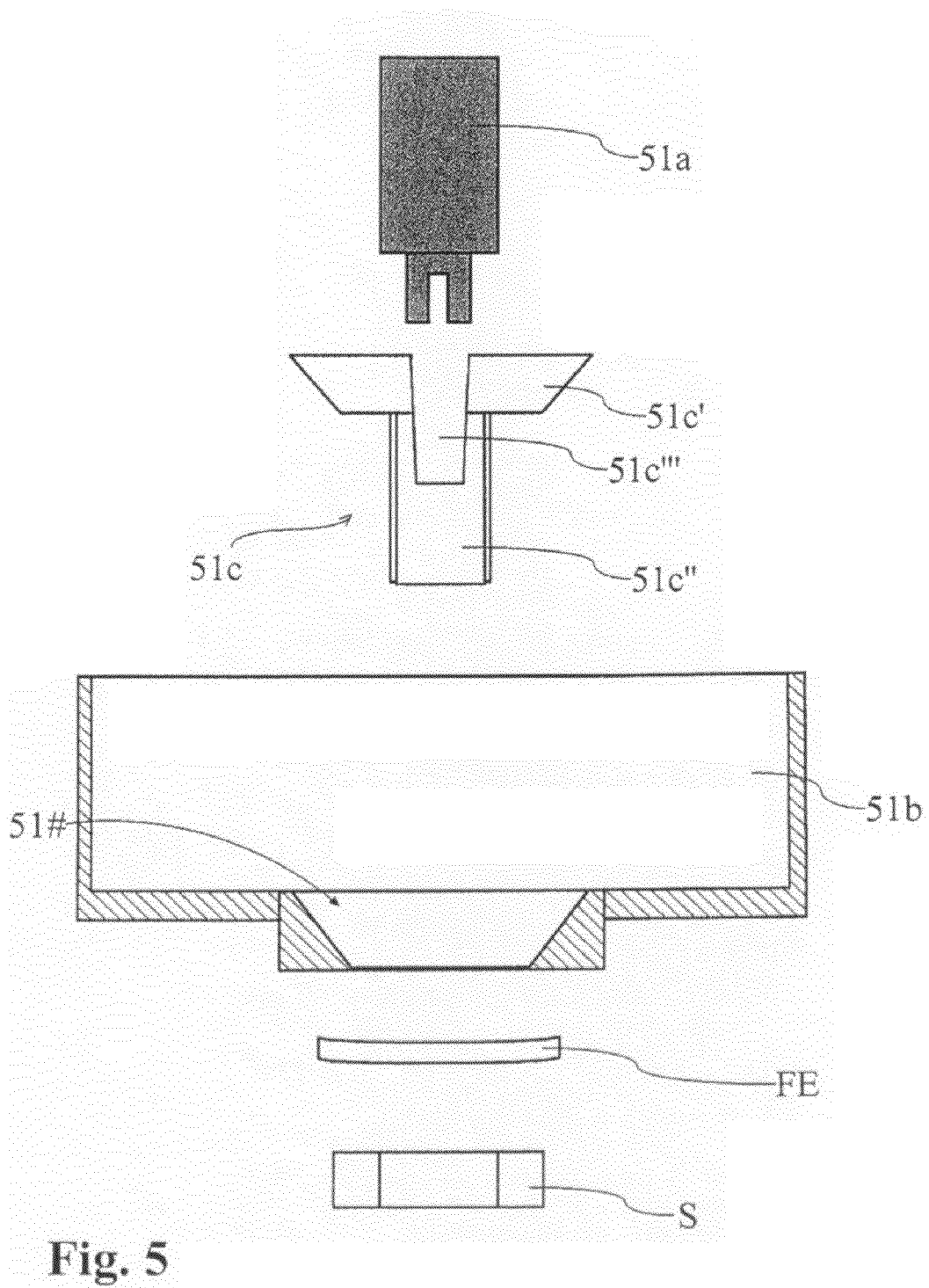
FIG. 5 shows schematically in exploded view, a magnet assembly of the invention.

In an additional embodiment of the invention, the retaining assembly is embodied as a clamping jaw gripping the permanent magnet. For such purpose, the retaining head, such as directly evident from the combination the FIG. 2a and 2b, or 5, is implemented by means of two, or also by means of a plurality of, head parts 51cA, 51cB, or 51cC, constructed, in each case, as a clamping jaw. The permanent magnet 51a is, in such case, such as directly evident from the combination of FIGS. 2a, b and 5, or FIGS. 3a, b and 5, placed with one of its ends between the at least two head parts 51cA, 51cB, while the at least two head parts are held pressed in each case against the permanent magnet 51a to form a—here, with interaction of clamping nut and passageway as well as the head parts, forced—force-based interlocking between retaining head 51c' and the therein ultimately clamped, permanent magnet 51a. At least for this case, it is additionally provided, that the retaining bolt has, as also schematically presented in FIG. 5, in a section following on the retaining head 51c', a section which is, in given cases, also provided at least partially with external thread ET, at least one longitudinal slot 51c''' extending essentially in the direction of the longitudinal axis of the retaining bolt 51c'' up to an edge of the retaining head 51c' facing the permanent magnet 51a. The longitudinal slot 51c''' is, in the case of assembled magnet assembly 5, slightly pressed together, under action of the clamping nut S as well as the passageway 51# acting against the head parts. In case required, additionally also the permanent magnet can, as schematically presented also in FIG. 5, have in its end region held in the installed state by the head parts an equally axially extending longitudinal slot, which is somewhat pressed together in the installed state. For implementing an as strong as possible, force-based interlocking between permanent magnet 51a and the thereagainst pressing, head parts 51cA, 51cB, as well as also for simplifying the mounting of the magnet assembly 5, it is additionally provided, that the inner surfaces of the head parts serving as clamping jaws for contacting the permanent magnet 51a have a contour essentially complementary to the contacted outer surface of the permanent magnet 51a, so that permanent magnet 51a and retaining head contact one another with as large surface as possible and so the therebetween acting, lastly the force-based interlocking creating, frictional forces are increased. For additional increasing of the withdrawal, or vibration, resistance between permanent magnet 51a and retaining assembly 51c, contours can be provided in their mutually contacting surfaces, for example, embodied as screw threads or annular grooves for instance, according to the manner provided in U.S. Pat. No. 7,299,699, for giving, additionally, supplemental, shape interlocking.

The invention claimed is:

1. A magnet assembly, comprising:
a permanent magnet, for delivering a magnetic field;
a retaining assembly, fixedly connected with said permanent magnet, by interlocking and/or by material bond, and having a retaining head facing said permanent magnet for holding said permanent magnet, and a retaining bolt affixed to said retaining head; and
a magnet cup having a cup floor
a cup wall extending from said cup floor, wherein:
said retaining head of said retaining assembly is accommodated at least partially in a passageway provided in the cup floor, and
an outer contact surface of said retaining head and an inner contact surface of the passageway contact one another to form a force-based interlocking between said magnet cup and said retaining assembly.

2. The magnet assembly as claimed in claim 1, wherein:
said retaining bolt of said retaining assembly has an external thread; and
said retaining head of said retaining assembly is held pressed against said cup floor by means of a clamping nut screwed onto said retaining bolt.

3. The magnet assembly as claimed in claim 2, wherein:
between said clamping nut and said cup floor, a resilient, or spring, element is placed.

4. The magnet assembly as claimed in claim 1, wherein:
said retaining head is formed by means of at least two, or more, head parts formed, in each case, as a clamping jaw.

5. The magnet assembly as claimed in claim 4, wherein:
said permanent magnet is placed with one of its ends between said at least two head parts; and
said at least two head parts are, in each case, held pressed against said permanent magnet to form a force-based interlocking between said permanent magnet and said retaining head.

6. The magnet assembly as claimed in claim 1, wherein:
the force-based interlocking between said magnet cup and said retaining assembly is produced by thermal shrink fitting said magnet cup onto said retaining assembly.

7. The magnet assembly as claimed in claim 1, wherein:
said permanent magnet and said retaining head are affixed to one another by means of, releasable, force-based interlocking and/or shape interlocking and/or by means of material bond.

8. The magnet assembly as claimed in claim 1, wherein:
said cup wall of said magnet cup has at least one slot.

9. The magnet assembly as claimed in claim 1, wherein:
said permanent magnet is composed at least partially, of a rare earth, and/or
said permanent magnet is composed at least partially.

10. The magnet assembly as claimed in claim 1, wherein:
said magnet cup is composed at least partially of a steel and/or
said magnet cup is composed at least partially of ferrite.

11. A measuring transducer of the vibration type for a medium flowing in a pipeline, which measuring transducer comprises:
at least one measuring tube vibrating at least at times for conveying medium to be measured; and
at least one oscillation transducer for vibrations of said at least one measuring tube or said oscillation transducer being held at said at least one measuring tube, wherein said at least one oscillation transducer includes a magnet assembly.

12. The measuring transducer as claimed in claim 11, wherein:
said magnet assembly is mechanically coupled via a retaining bolt with the at least one measuring tube.

13. The measuring transducer as claimed in claim 11, wherein:
said at least one oscillation transducer further includes a cylindrical coil exposed to the magnetic field of a permanent magnet.

14. The use of a measuring transducer as claimed in claim 11 in an in-line measuring device for measuring and/or monitoring at least one parameter, especially a mass flow, m, a density, $\rho$, and/or a viscosity, $\eta$, of a medium flowing in a pipeline, especially a Coriolis mass flow measuring device, a density measuring device, a viscosity measuring device, or the like, especially in the case of an operating temperature of, at least at times, more than 200° C. and/or, at least at times, less than −50° C.

15. The measuring transducer as claimed in claim 11, wherein said magnetic assembly includes:
- a permanent magnet, for delivering a magnetic field;
- a retaining assembly, fixedly connected with said permanent magnet, by interlocking and/or by material bond, and having a retaining head facing said permanent magnet for holding said permanent magnet, and a retaining bolt affixed to said retaining head, and
- a magnet cup having a cup floor
- a cup wall extending from said cup floor, tubularly;
- said retaining head of said retaining assembly is accommodated at least partially in a passageway provided in the cup floor, and
- an outer contact surface of said retaining head and an inner contact surface of the passageway contact one another to form a force-based interlocking between said magnet cup and said retaining assembly.

* * * * *